(12) United States Patent
Wickert et al.

(10) Patent No.: US 6,291,202 B1
(45) Date of Patent: *Sep. 18, 2001

(54) DISC ASSAY DEVICE WITH INOCULATION PAD AND METHODS OF USE

(75) Inventors: Peter D. Wickert, St. Paul; Michael G. Williams, Vadnais Heights, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/645,952

(22) Filed: Aug. 25, 2000

Related U.S. Application Data

(63) Continuation of application No. 09/264,804, filed on Mar. 9, 1999.

(51) Int. Cl.[7] .................. C12Q 1/04; C12Q 1/00
(52) U.S. Cl. .............. 435/34; 435/4; 435/283.1; 422/50
(58) Field of Search ................ 435/34, 4, 283.1; 422/50

(56) References Cited

U.S. PATENT DOCUMENTS

| | | | |
|---|---|---|---|
| 3,010,880 | 11/1961 | Littman et al. | 195/103.5 |
| 3,509,026 | 4/1970 | Sanders | 195/103.5 |
| 3,856,628 | 12/1974 | Sbarra | 195/103.5 R |

(List continued on next page.)

FOREIGN PATENT DOCUMENTS

| | | | |
|---|---|---|---|
| 32 26 407 C2 | 5/1985 | (DE) | G01N/31/20 |
| 36 31 066 A1 | 4/1988 | (DE) | B01L/3/00 |
| 37 32 142 A1 | 4/1989 | (DE) | C12M/3/00 |
| 42 18 917 A1 | 12/1993 | (DE) | C12N/1/34 |
| 0 321 736 B1 | 2/1989 | (EP) | G01N/33/53 |
| 0 459 093 A2 | 12/1991 | (EP) | C12M/1/32 |
| 0 496 200 A2 | 7/1992 | (EP) | C12M/1/32 |
| 0 656 420 A1 | 6/1995 | (EP) | C12Q/1/00 |
| 0 751 393 A2 | 1/1997 | (EP) | G01N/33/49 |
| 0 795 600 A1 | 7/1997 | (EP) | C12M/1/34 |
| 0 795 600 A1 | 9/1997 | (EP) | C12M/1/34 |
| 0 834 729 A2 | 4/1998 | (EP) | G01N/21/03 |
| 0 928 830 A1 | 7/1999 | (EP) | C12M/1/34 |
| 1 437 404 | 5/1976 | (GB) | C12K/1/10 |
| 63 096558 | 4/1988 | (JP) | G01N/33/543 |
| 04 051890 | 2/1992 | (JP) . | |
| 04 051900 | 2/1992 | (JP) . | |
| 04 265860 | 9/1992 | (JP) | G01N/33/543 |
| 06 062893 | 3/1994 | (JP) . | |
| 08 000286 | 1/1996 | (JP) | C12Q/1/00 |
| 08 140664 | 6/1996 | (JP) . | |
| 09 019282 | 1/1997 | (JP) . | |
| WO 92/12257 | 7/1992 | (WO) | C12Q/1/02 |
| WO 93/11727 | 6/1993 | (WO) | A61F/13/15 |
| WO 93/19199 | 9/1993 | (WO) | C12Q/1/06 |
| WO 94/11489 | 5/1994 | (WO) | C12M/1/14 |
| WO 95/23026 | 8/1995 | (WO) | B01L/3/00 |
| WO 96/14432 | 5/1996 | (WO) | C12Q/1/20 |
| WO 96/15435 | 5/1996 | (WO) . | |
| WO 96/40980 | 12/1996 | (WO) | C12Q/1/04 |
| WO 97/05274 | 2/1997 | (WO) | C12Q/1/22 |
| WO 97/08291 | 3/1997 | (WO) | C12M/1/00 |
| WO 97/12242 | 4/1997 | (WO) | G01N/33/52 |
| WO 97/13839 | 4/1997 | (WO) | C12M/3/00 |

(List continued on next page.)

OTHER PUBLICATIONS

Product Brochure: SimPlate™ Total Count Plate from Idexx Laboratories, Inc., undated.

*Primary Examiner*—Louise N. Leary
(74) *Attorney, Agent, or Firm*—Robert W. Sprague

(57) ABSTRACT

An assay device for detection and enumeration of microorganisms. The device includes absorbent discs on a substrate, an inoculation vehicle to inoculate the discs with sample and an optional coversheet. Methods of use are also disclosed.

15 Claims, 5 Drawing Sheets

U.S. PATENT DOCUMENTS

| | | | |
|---|---|---|---|
| 3,881,993 | 5/1975 | Freake et al. | 195/139 |
| 3,929,583 | 12/1975 | Sharpe et al. | 195/127 |
| 4,018,652 | 4/1977 | Lanham et al. | 195/103.5 M |
| 4,264,560 | 4/1981 | Natelson | 422/58 |
| 4,335,206 | 6/1982 | Wilikins et al. | 435/34 |
| 4,485,171 | 11/1984 | Ikeda et al. | 435/30 |
| 4,682,891 | 7/1987 | de Macario et al. | 356/244 |
| 4,777,021 | 10/1988 | Wertz et al. | 422/101 |
| 4,803,154 | 2/1989 | Uo et al. | 435/7 |
| 4,806,316 | 2/1989 | Johnson et al. | 422/100 |
| 4,906,439 | 3/1990 | Grenner | 422/56 |
| 5,219,462 | 6/1993 | Bruxvoort et al. | 51/293 |
| 5,229,163 | 7/1993 | Fox | 427/2 |
| 5,235,827 | 8/1993 | Sussman et al. | 435/34 |
| 5,338,666 | 8/1994 | Monthony et al. | 435/34 |
| 5,409,838 | 4/1995 | Wickert | 436/8 |
| 5,457,030 | 10/1995 | Badal et al. | 435/34 |
| 5,494,823 | 2/1996 | Takemoto et al. | 435/287.4 |
| 5,498,525 | 3/1996 | Rees et al. | 435/29 |
| 5,503,803 | 4/1996 | Brown | 422/102 |
| 5,700,655 | 12/1997 | Croteau et al. | 435/30 |
| 5,707,799 | 1/1998 | Hansmann et al. | 435/6 |
| 6,174,699 * | 1/2001 | Wickert et al. | 435/34 |

FOREIGN PATENT DOCUMENTS

| | | | |
|---|---|---|---|
| WO 97/18455 | 5/1997 | (WO) | G01N/1/00 |
| WO 97/24432 | 7/1997 | (WO) | C12M/1/34 |
| WO 97/37036 | 10/1997 | (WO) | C12Q/1/08 |
| WO 97/49987 | 12/1997 | (WO) | G01N/27/02 |
| WO 98/31466 | 7/1998 | (WO) | B01L/11/00 |
| WO 98/45406 | 10/1998 | (WO) | C12M/1/20 |
| WO 99/06589 | 2/1999 | (WO) | C12Q/1/02 |
| WO 99-32601 | 7/1999 | (WO) | C12M/1/20 |

* cited by examiner

DISC ASSAY DEVICE WITH INOCULATION PAD AND METHODS OF USE

This is a continuation of application Ser. No. 09/264,804 filed Mar. 9, 1999.

FIELD

This invention relates to disc devices and methods of use for detecting and enumerating microorganisms present within a sample.

BACKGROUND

The detection and enumeration of microorganisms is practiced in numerous settings, including the food-processing industry (testing for the contamination of food by microorganisms such as *E. coli* and *S. aureus*), the health care industry (testing of patient samples and other clinical samples for infection or contamination), environmental testing industry the pharmaceutical industry, and the cosmetic industry.

Growth-based detection and enumeration of microorganisms is commonly practiced using either liquid nutrient media (for example, most probable number analysis (MPN)) or semi-solid nutrient media (agar petri dishes). Enumeration using the liquid MPN method is typically achieved by placing serial 10-fold dilutions of a sample of interest in replicate sets of tubes containing selective media and chemical indicators. The tubes are incubated for 24–48 hours at elevated temperatures (30–37° C.) followed by examination for growth of organisms. A statistical formula based on the volume of sample tested and the number of positive and negative tubes for each set, is used to estimate the number of organisms present in the initial sample.

This method of performing MPN analysis has several disadvantages. It is labor intensive because of the multiple diluting and pipetting steps necessary to perform the analysis. Typically, it is only practical to use replicate sets of about three to five tubes for each dilution. As a result, the 95% confidence limits for an MPN estimate for microbial concentration are extremely wide. For example, a three tube MPN estimate of 20 has 95% confidence limits ranging from 7 to 89. Furthermore, results typically are not obtainable in less than twenty-four hours.

Multi-well devices have been introduced for use in connection with MPN analysis. A user inoculates the device by introducing a sample of the item to be tested, such as food, onto the substrate containing the wells. Typically, the sample includes growth media and indicators. Once inoculated, the user incubates the device and then calculates the MPN based on the number of "positive" wells.

Multi-well devices present many potential problems. Inoculation may be hampered by air bubbles that form in the wells during introduction of the sample. Each well may not receive the same volume of sample. Furthermore, the method of inoculation or the device may promote bridging and cross-contamination among the wells, thereby potentially adversely affecting the MPN calculation.

Another potential problem with multi-well devices is that they may be inconvenient to use. For example, most multi-well devices are inoculated by either pipetting sample directly into the wells or pouring sample onto the multi-well substrate. Pippetting is labor and time intensive. Pouring requires that the wells be evenly filled and that excess sample be poured off. In either event, these devices may lend themselves to contamination by outside sources during the inoculation procedure.

SUMMARY

The present invention addresses many of the disadvantages of the prior art. The invention provides assay devices and methods for the rapid detection and enumeration of microorganisms. The device has a substrate including absorbent discs attached thereto and an inoculation vehicle attached to the device, positioned to inoculate the absorbent discs. Optionally, the device may include a coversheet.

In one aspect of the present invention, the substrate includes two different sizes of discs. Preferably, the substrate includes about fifty discs of one size and fifty discs of a different size. In a particularly preferred embodiment, the substrate includes discs capable of holding about two microliters of sample and discs of a different size capable of holding about sixteen microliters of sample and the sixteen microliter discs at least partially surround the two microliter discs. The substrate may further be hydrophobic to assist in preventing cross-contamination between discs.

The device may optionally include an outer edge or margin defining a space between the discs and the end of the substrate. The outer edge or margin may optionally be raised. Preferably, the outer edge or margin is sized to permit the optional coversheet to seal to the substrate when the device is in use.

In another aspect of the present invention, the inoculation vehicle is an absorbent inoculation pad with a backing attached thereto. Preferably, the backing is detachably attached to the device along a perforation.

In another aspect of the present invention, the coversheet is attached to the substrate to form a hinge. The inoculation vehicle may be adhesively attached to the hinge in such a way that the inoculation vehicle is capable of inoculating the absorbent discs.

In a method of the present invention, an assay device as described above is provided. The user places the sample to be tested on the inoculation vehicle and places the inoculation vehicle against the absorbent discs, thereby resulting in the discs being inoculated with sample. The user removes and discards the inoculation vehicle and incubates the device. The user then conducts detection of any target microorganisms that grew during incubation and may subsequently enumerate the microorganisms. In a preferred embodiment, the method may be conducted in twenty-four hours or less.

The present invention overcomes many of the deficiencies of the devices and methods of the prior art. The device may be inoculated quickly and evenly and virtually simultaneously, without concern about air bubbles forming. The detachable inoculation vehicle is easily detached and disposed of. Once detached, the inoculation vehicle does not remain with the device and therefore does not present a possible source of contamination. The coversheet provides additional protection against contamination and helps prevent drying out of the discs.

In the case of MPN analysis for the detection and enumeration of microorganisms, the approaches described herein allow for the use of water-soluble indicator species, and reduce or eliminate the need for the several dilutions typically required in current MPN analysis.

Other advantages of the invention will be apparent from the following detailed description and the figures.

DETAILED DESCRIPTION

This invention relates to disc devices and method of use thereof for conducting signal-based detection and enumeration of microorganisms.

For the purposes of the present invention, the following terms shall have the meanings defined:

"Attach" shall mean adherence of the discs to the substrate by any method or means known in the art at the time of manufacture thereof, including using adhesive, ultrasonic welding, embossing, or physical attachment.

"Cover" when used as a verb, shall not be limited to a particular spatial orientation, such as covering the top a device.

"Disc" shall not be limited as to shape or configuration. For example, the discs may be of circular, oval, square, or polygonal shape, or other appropriate shapes.

"Hydrophobic" and "hydrophilic" are herein given the meanings commonly understood in the art. Thus, a "hydrophobic" material has relatively little or no affinity for water or aqueous media, while a "hydrophilic" material has relatively strong affinity for water or aqueous media.

"Inoculation" shall mean wetting an absorbent disc(s) of the present invention with sample.

"Microorganism" shall mean all microscopic living organisms and cells, including without limitation bacteria, mycoplasmas, rickettsias, spirochetes, yeasts, molds, protozoans, as well as microscopic forms of eukaryotic cells, for example single cells (cultured or derived directly from a tissue or organ) or small clumps of cells. Microorganisms are detected and/or enumerated not only when whole cells are detected directly, but also when such cells are detected indirectly, such as through detection or quantification of cell fragments, cell-derived biological molecules, or cell by-products.

Figure 1:
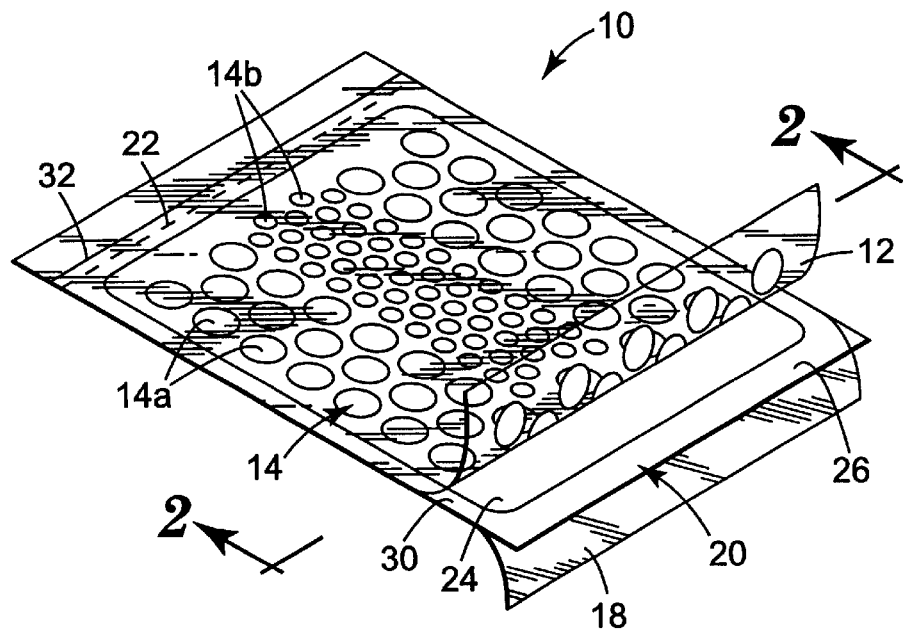
FIG. 1 is a perspective view of a device of the present invention.
Figure 2:
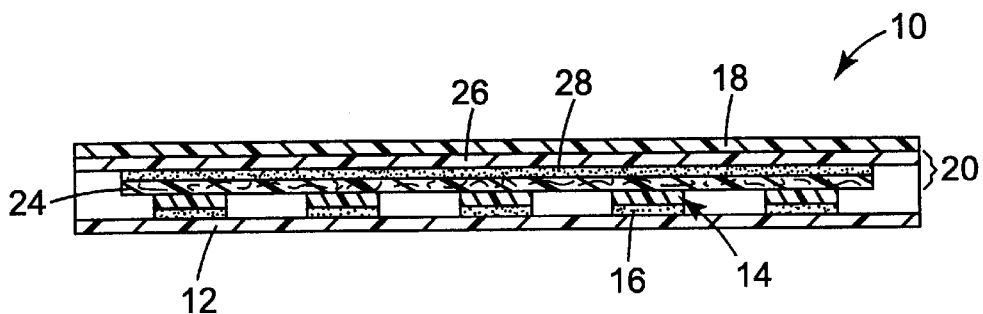
FIG. 2 is a cross section of the device, taken along the line 2—2 in FIG. 1, wherein the device has been rotated 180°.

With reference to FIGS. 1 and 2, the substrate 12 of the assay device 10 can be fabricated from any material that is relatively hydrophobic and provides a suitable surface or support for the discs 14 described below. Substrate 12 can be fabricated, for example, from polymeric films or other appropriate materials. Appropriate polymers include without limitation polyethylene, polypropylene, polyester, polyimides, fluoropolymers, polycarbonates, polyurethanes, and polystyrenes. The substrate 12 preferably does not exhibit substantial fluorescent or light-absorbing properties that would interfere with any fluorescent or color-based indicator system that may be employed for the purposes of detection. Preferably, the substrate 12 will not leach any chemicals upon contact with liquid sample.

The hydrophobicity of the substrate 12 assists in preventing cross-contamination of the discs 14. In this regard, the substrate 12 may be treated to impart hydrophobicity. For example, a thin layer of acrylated silicone or other hydrophobic material may be added to the substrate 12. Those skilled in the art will recognize other means to impart surface hydrophobicity.

Absorbent discs 14 are attached to the substrate 12 for holding and retaining liquid sample. Accordingly, the discs 14 may be constructed from a variety of absorbent materials, including cellulosics, polyolefins, polyesters, and polyamides, with cellulosics being preferred. Suitable cellulosics include paper, wood pulp and rayon and may include chemically modified cellulosics, such as cellulose esters. Suitable polyolefins include hydrophilic polyethylene or hydrophilic polypropylene fibers. Suitable polyamides include nylon. Suitable polyesters include polylactic acid.

The absorbent discs 14 of the assay device 10 preferably are of uniform size and each disc has a liquid-retention capacity of about one tenth of a microliter to about one hundred microliters of the liquid sample. More preferably, each disc has a liquid retention capacity of about two microliters to about sixteen microliters. Typically, the higher the total volume retention of sample, the greater the sensitivity of the device 10. Accordingly, it is desirable to retain a high volume of sample. The device 10 may include numerous discs 14. The assay device 10 preferably contains between one and about six hundred discs, with about one hundred discs being most preferred.

The discs 14 may be attached to the substrate 12 by various means known in the art, including without limitation, by using an adhesive 16 or two-sided tape. Preferred adhesives include water-insoluble isooctyl acrylate adhesives as disclosed in U.S. Pat. No. 5,409,838, the disclosure of which is incorporated herein by reference. An example of a suitable two-sided tape is available under Product Number 1513, Double Stick Tape™, available from 3M Co., St. Paul, Minn. The discs 14 are attached to the substrate 12 sufficiently far apart that sample, once inoculated onto a disc 14, does not wick directly from that disc to another.

The device 10 also may preferably contain sets of discs 14 with differing volumes. Having discs with differing volumes could dramatically broaden the effective counting range of the device in an MPN analysis, as would be readily appreciated by one skilled in the art. In this preferred embodiment, the device 10 preferably includes about one hundred discs. Most preferably, the device 10 includes about fifty discs with a liquid-retention volume of about sixteen microliters and about fifty discs with a liquid-retention volume of about two microliters.

If discs 14 of more than one size are present, it is preferred that the larger discs 14a substantially surround the smaller discs 14b, such as illustrated in FIG. 1. The larger discs 14a are located between the smaller discs 14b and the outer margin 30 of substrate 12. It is believed that placement of the discs 14 in this manner assists in preventing the smaller discs 14 from drying out because the larger discs 14a act to humidify the area of the smaller discs 14b, as well as partially shield smaller discs 14b from airflow that may dry the smaller discs 14b, such as may occur during elevated temperature incubation. With reference to Example 3, below, in order to achieve this result, it is not necessary that the larger discs 14a completely surround the smaller discs 14b, either with respect to the smaller discs 14b themselves or the outer margin.

The discs 14 may be of any size, shape and height. Preferably, the discs 14 are of uniform height. The height may be adjusted to permit the optional coversheet 18 to seal with the substrate, as described more fully below.

Figure 3:
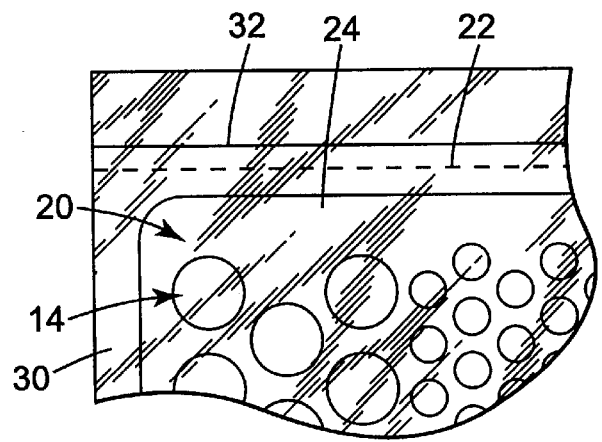
FIG. 3 is a partial top plan view of a device of the present invention, detailing a detachable inoculation vehicle.

With reference to FIGS. 1–3, the present invention 10 includes an inoculation vehicle 20. The inoculation vehicle 20 is capable of retaining sample for subsequent inoculation of the absorbent discs 14. Examples of possible inoculation vehicles 20 include absorbent pads, thermoformed plates, and reservoirs.

With reference to FIG 3, the inoculation vehicle 20 is attached to the device on manner permit the vehicle 20 to come into contact with the absorbent discs 14. A preferred method is to attach the inoculation vehicle 20 along a perforation 22. In this configuration, the inoculation vehicle 20 may be removed from the device 10 after use simple by tearing along the perforation 22. The vehicle 20 substantially covers the area of the substrate 12 having discs 14.

Sample distributes throughout or within the vehicle 20 upon placement of a sample thereon. Subsequently, the user places the inoculation vehicle 20 in contact with the discs 14. Sample transfers from the vehicle 20 and into the discs 14, virtually simultaneously and evenly.

Preferably, the inoculation vehicle 20 is an absorbent inoculation pad 24 with a backing 26 attached thereto. The pad 24 may be made of any number of absorbent materials, such as those listed above for the discs material. For manufacturing purposes, it is desirable that the pad 20 be constructed of the same material as the discs 14. The pad 24 may be any size or shape. Preferably, the pad 24 covers more area of the substrate 12 than that covered by the discs 14 and covers all of the discs 14 to ensure that all of the discs 14 are capable of being inoculated when the pad 24 is placed in contact with the discs 14.

The backing 26 attaches to the substrate 12. Preferably, the backing 26 is attached in a detachable manner, such as along a perforation 22. Preferred backings 26 are relatively thin and do not leach chemicals upon contact with liquid sample. For manufacturing purposes, the backing 26 may be manufactured from the same material as the substrate 12.

The pad 24 may be attached to the backing 26 in any number of ways known in the art, such as with adhesive 28. Preferably, the backing, 26 is attached in a manner that does not result in leaching of chemicals upon contact with a liquid sample.

Optionally, the device 10 may include a coversheet 18 to protect the discs 14 from contamination or desiccation once sample has been added to the device 10. The coversheet 18 may be constructed of any number of materials. Preferably, the coversheet 18 is flexible, transparent to the extent one may conduct detection through the coversheet 18, compatible with growing microorganisms and the detection system to be used in the device (e.g. does not exhibit luminescence or fluorescence, or opacity to the degree that would substantially interfere with detection), and does not leach undesirable chemicals upon coming into contact with liquid sample.

Figure 4:
FIG. 4 is an end view of a device of the present invention after the inoculation vehicle of the device has been removed.

With reference to FIG. 4, the coversheet 18 is attached to the device 10 in such as way that it covers substantially all of the discs 14 and preferably covers all of the discs 14. Preferably, the coversheet 18 and the substrate 12 are sized to permit the coversheet 18 to contact and seal to the substrate 12 in use. For purposes of this application, to "seal" does not require that the connection between the substrate 12 and coversheet 18 be airtight. Instead, coversheet 18 overlays and comes into substantial contact with the substrate 12 to assist in preventing contamination during use and in reducing drying out of the discs 14.

With reference to FIG. 1, the coversheet 18, substrate 12 and inoculation vehicle 20 may be attached to each other at one end of the device to form a hinge 32. In this configuration, preferably, the inoculation vehicle 20 is attached between the coversheet 18 and the substrate 12.

The liquid test sample may be any sample of interest, from any source. The liquid test sample may include selective nutrient growth media for the microorganism of interest, and/or an indicator substance that produces a signal in the presence of the growing microorganism. Optionally, the nutrient media may include a gelling agent that assists in "encapsulating" the growing microorganisms. Such gelling agents are known to those of skill in the art, and include any water-absorbing material that becomes a gel upon addition of an aqueous liquid.

Preferably, nutrient growth media is present as a coating or other deposition within or on the absorbent discs, in amounts sufficient to achieve desired concentrations when a volume of the liquid test sample is distributed into the disc. Such a coating may be achieved, for example, by placing or distributing a solution of the nutrient media (with or without gelling agent) onto the discs and drying the solution to produce a coating or deposition of the nutrient medium on the discs. Components of the media may be present in the adhesive or other substance that binds the discs to the substrate (if applicable). The media ultimately diffuses into the sample.

A wide variety of selective growth media for a wide variety of microorganisms of interest is known, as is a wide variety of indicator substances for a wide variety of microorganisms, and any of these media or indicator substances is suitable for use in the method of the invention. An advantage of the present invention is that soluble indicators can be used, since diffusion is prevented by confinement of the aqueous biological sample in the absorbent discs.

Other assay reagents may be coated or otherwise deposited within the absorbent discs of the assay devices. Such assay reagents may include, without limitation, gelling agents and indicator substances such as chromogenic, fluorescent, fluorogenic, luminescent, and electrochemical indicator. The assay reagents can be immobilized in the absorbent discs by any of numerous methods for immobilizing assay reagents on solid substrates known to those of skill in the art. Such methods include for example drying down assay reagent-containing liquids in the discs, as well as other methods for noncovalently attaching biomolecules and other assay reagents to a solid substrate. Alternatively, various methods may be employed to covalently attach assay reagents to the discs by methods well known to those of skill in the art.

In the present invention, fluorogenic indicators are preferred because they may be detected at relatively low concentrations. Suitable indicators include 4-methylumbelliferyl phosphate, and 4-methylumbelleferyl-B-D-glucopyranoside, L-phenylalanine-7-amido-4-methylcoumarine. Other may include 4-methylumbelliferyl acetate and 4-methylumbelliferyl sulfate.

The materials of the present invention preferably are biocompatible and may be used with fluorescent indicators. The materials do not exhibit significant inherent fluorescence that would interfere with the use of the indicators. In addition, the discs preferably do not exhibit significant absorption at the emission wavelength of the indicators employed.

In the method of the present invention, a liquid sample for testing is prepared. In addition to the food, water, etc. to be tested, the sample may include indicators and other reagents. The user selects a device 10 having growth media selective for the target microorganism.

With reference to FIG. 1, in order to begin the process, the user exposes the inoculation vehicle 20 and places sample on the vehicle 20. Sample may be placed on the vehicle 20 by pouring, pipetting, or other suitable means.

In the event an absorbent vehicle 20 is used, it is preferred to place enough sample on the vehicle 20 to substantially saturate both the vehicle 20 and the absorbent discs 14. Under these circumstances, the absorbent vehicle 20 retains a liquid volume beyond the liquid saturation level of the absorbent vehicle 20. This excess liquid volume appears to assist in distributing the quickly throughout the pad 24 prior to the inoculation of the discs 14.

With continuing reference to FIG. 1, the user places the inoculation vehicle 20 into contact with the discs 14 such that sample transfers from the vehicle 20 to the discs 14. Preferably, the vehicle 20 is of such a size as to cover the area of the substrate 12 having the discs 14. The user applies pressure to the vehicle 20 to assist in the transfer of sample from the vehicle 20 to the discs 14. For example, moderate pressure can be applied by pressing down on the outside of the device with a plastic spreader. This method results in a near simultaneous inoculation of the discs 14. Each disc 14 becomes substantially saturated and for each size disc 14, contains approximately the same amount of sample.

This method of inoculation, coupled with the construction of the device, substantially prevents cross contamination between discs 14. The discs 14 rapidly absorb sample, thereby minimizing the volume of sample that distributes to the substrate 12. The hydrophobicity of the substrate 12 helps ensure that sample does not cross-contaminate the discs 14 once inoculation occurs.

After inoculation, the inoculation vehicle 20 may be removed and discarded. In a preferred embodiment, the vehicle 20 is an absorbent inoculation pad 24 with a backing 26. The backing 26 is attached to the device along a perforation 22. After inoculation, the backing 26 with pad 24 is simply form from the device 10 and discarded. If a coversheet 18 is included, it is placed over the discs 14 and seals to the substrate 12, as depicted in FIG. 4. Alternatively, the device 10 may be incubated in an enclosure, bag, or other vessel to prevent drying out and/or contamination of the discs 14.

After distribution of the sample from the vehicle 20 to the discs 14, various assays may be carried out depending on desired uses. For microbial detection or enumeration, the assay device may be incubated for a time sufficient to permit at least one cell division cycle of the microorganisms. For these purposes, the device 10 is generally incubated at about 25° C. to about 45° C., more preferably at about 30° C. to about 37° C. The incubation time for microorganisms detection will vary. The detection time will also vary depending on the growth rate and the number of microorganisms present in the sample. Taking into account these considerations, detection time for purposes of enumeration may be as little as about 6–8 hours. This relatively short incubation time represents a distinct advantage over detection methods currently used, which typically require incubation times of about 24 hours or more.

Following incubation of the assay device, the present or absence of the microorganism in discs (and thus in the liquid test sample) is detected. The mode of detection depend on the type of indicator substance used in the method. Any indicator substance that is capable of providing a detectable signal may be used. Such indicators include but are not limited to fluorescent, chromogenic, luminescent, and electrochemical indicators. The presence or absence of a microorganism in a disc can be visually detected, with the naked eye or miroscopocally, if a chromogenic or luminescent indicator is used. The indicator may be coated or otherwise incorporated into the discs. The indicators may also be included in the adhesive or other substance that binds the discs (if applicable) to the substrate. In this instance, the indicator ultimately diffuses into the liquid sample. If a fluorescent indicator substance is used, equipment and methods for detecting a fluorescent signal may be employed for detection. These are numerous indicator substances and signal detection systems, including systems for detecting electrochemical changes, known in the art for detecting microorganisms, any such substance or system may be used in accordance with the present invention.

The detection of microorganisms in the liquid sample may further involve the enumeration of a microorganism count in the liquid test sample. A particularly useful application of these methods and devices is growth-based enumeration of microorganisms in liquid test samples. Such enumeration is very important in the testing of food, environmental, clinical, pharmaceutical, cosmetic, and other samples for contamination by microorganisms. The methods and devices of this invention allow for the efficient, accurate, convenient, and cost-effective testing of such samples. A preferred use of the methods and devices of this invention in such microbiological testing is in MPN enumeration techniques. In traditional MPN analysis, a sample of interest is serially diluted (10 fold) and pipetted in equal amounts into replicate sets of tubes containing selective growth media and chemical indicators. The tubes are incubated at elevated temperature for about 24–48 hours followed by examination for growth of organisms. A statistical formula, based on the volume of the sample and the number of positive and negative tubes for each set, is used to estimate the number of organisms present (per volume) in the initial sample. As currently used, this traditional method has several disadvantages. It is labor intensive because of the multiple diluting and pipetting steps required to perform the analysis. As a practical matter, only replicate sets of about three to five tubes for each dilution are commonly used. As a result, the 95% confidence limits for an MPN estimate of microbial concentration using this method are extremely wide. For example, a nine tube (3ten-fold dilutions) MPN estimate of 20 has 95% confidence limits ranging from 7 to 89.

The use of the methods and devices of the present invention in MPN analysis overcomes several of the above-noted disadvantages. The amount of labor is greatly reduced because no pipetting into individual tubes is necessary, and very little or no agitation or other manipulations are required. Instead, the liquid sample is distributed to absorbent discs using an inoculation vehicle. In addition, fewer sample dilutions are necessary when large numbers of absorbent discs are present in the device. The relatively large number of absorbent discs also provides a more accurate estimate of microbial concentration. This is because the correspondingly larger number of sample aliquots provides a corresponding narrower confidence limit interval.

The methods of the present invention may be automated and the devices may be analyzed using an automated system.

All references and publications cited herein are expressly incorporated herein by reference into this disclosure. Particular embodiments of this invention will be discussed in detail and reference has been made to possible variations within the scope of this invention. These are a variety of alternative techniques and procedures available to those of skill in the art that would similarly permit one to successfully practice the intended invention.

EXAMPLES

The following examples are offered to aid in understanding of the present invention and are not to be construed as limiting the scope thereof. Unless otherwise indicated, all parts and percentages are by weight.

Example 1

Absorbent Disc Assay Devices

Absorbent disc assay devices having an inoculation vehicle and capable of being used for the detection and enumeration of microorganisms in a liquid test sample were constructed as described in this example.

A sheet of absorbent nonwoven cellulosic material (Product Grade 10201, Dexter, Windsor Locks, Conn.) was laminated to a Rexam silicone-coated polyester film (Grade 15819, 2-mil thick, Rexam Release, West Chicago, Ill.) with an isooctyl acrylate/acrylamide (96/4 weight ratio) pressure sensitive adhesive (PSA). The material was saturated with an aqueous broth containing the growth nutrients and indicator chemicals listed in Table 1. Excess liquid was removed and the laminate was dried at about 110° C. for about 10 minutes. Circular disc were then cut into the dried laminate using a controlled depth die that cut only through the absorbent material and adhesive layers. The non-disc material was then removed from the laminate and discarded to provide a sheet of the film containing an array of circular disc. The discs were of two sizes: small discs approximately 4.1 mm in diameter and large discs approximately 8.3 mm in diameter; and were grouped and spaced apart as illustrated in FIG. 1. Based on gravimetric measurements, the small and large discs had capacities to retain about 2 and 16 microliters of liquid, respectively. The disc-containing sheet was cut into 10.9-cm×12.1-cm rectangles for use in construction of the assay devices. Each individual rectangular sheet contained 52 small discs grouped in parallel rows within a surrounding group of 50 large discs in parallel rows as illustrated in FIG. 1. The distance from the outer edge of the large discs to the edge of the rectangular sheet was about 1.4 cm.

An inoculation vehicle was prepared by adhering an 8.9-cm×9.5-cm pad of the absorbent nonwoven cellulosic material (Product Grade 10201, Dexter) to a 10.9-cm×13.7-cm rectangular sheet of the Rexam silicone-coated polyester film using the acrylate-based PSA described above. The film backing was perforated at one end (as shown in FIG. 3) to facilitate removal of the pad after inoculation.

The 10.9-cm end of the inoculation vehicle was adhered to the 10.9-cm end of the disc-containing sheet with two sided tape (Product 1513, 3M Co., St. Paul, Minn.) to form a hinge, such that the absorbent pad was aligned over and facing the absorbent discs. A 10.9-cm×13.2-cm sheet of biaxially-oriented polypropylene (BOPP) film (1.6-mil thick, 3M Co.) was then adhered with double sick tape to the hinge-edge of the inoculation vehicle to serve as a coversheet for the device. See FIGS. 1–3 for various views of the entire device in finished form. After construction was completed, the assay devices were gamma irradiated to a level of about 10 kGy.

TABLE 1

| Component | Concentration (g/l) |
|---|---|
| Sodium Pyruvate (Sigma Chemical Co., St. Louis, MO) | 4.4 |
| Tryptone (Difco Laboratories, Detroit, MI) | 7.5 |
| Yeast Extract (Difco Laboratories) | 2.5 |
| Glucose (Difco Laboratories) | 3.6 |
| $KH_2PO_4$ (Fisher Chemicals, Fair Lawn, NJ) | 1.08 |
| $Na_2HPO_4$ (Fisher Chemicals) | 5.97 |
| $MgSO_4 \cdot 7H_2O$ (Aldrich Chemical Co., Milwaukee, WI) | 0.98 |
| 4-Methylumbelliferylphosphate (Biosynth Int., Naperville, IL) | 0.05 |
| L-Alanine-7-amido-4-methylcoumarin (Biosynth Int.) | 0.05 |
| L-Phenylalanine-7-amido-4-methylcoumarin (Biosynth Int.) | 0.05 |

Example 2

Precision of the Inoculation Step

The objective of this example was to determine the reproducibility of transferring a liquid sample from the absorbent pad of the inoculation vehicle to the plurality of absorbent discs of an assay device.

An assay device constructed as described in Example 1 was inoculated with a sample (3.5 mil) of Butterfield's Buffer (Weber Scientific, Hamilton, N.J.) as follows. The assay device was placed on a hard, flat, level surface with the disc-containing film (disc-film) on the top. This film was lifted with one hand while the liquid sample was pipetted onto the central region of the inoculating pad. After waiting about 2–5 seconds for the sample to absorb into the pad, the disc-film was released and allowed to drop onto the pad-containing film (pad-film). A clear, flat plastic spreader was pressed against the disc-film to promote the transfer of liquid sample from the pad to the discs. This transfer of sample was evident by a darkening of the color of the discs. After inoculation of the discs, the inoculation pad was removed by tearing (at the perforation) the inoculation vehicle away from the hinge edge and then discarding the pad. Two other assay devices were inoculated in an identical manner to give a total to three replications.

Immediately after inoculation of the assay devices, the absorbency of light by each disc was measured with a Gretag AG Model D19C densitometer (Regensdorf, Switzerland). The background for the light absorbency readings was a strip of black electrical tape (SCOTCH™ Super 33+, 1.9-cm wide, 3M Co., St. Paul, Minn.). Light absorbency measurements were also taken from the discs of five uninoculated assay devices in order to calculate an average light absorbency for dry discs. The results are presented in Table 2.

TABLE 2

|  | Dry Discs | Inoculated Discs (Large) | Inoculated Discs (Small) |
|---|---|---|---|
| Number of Discs Analyzed | 52 | 150 | 156 |
| Light Absorbency (Average) | 0.328 | 0.668 | 0.645 |
| Standard Deviation | 0.023 | 0.083 | 0.027 |

The relatively small standard deviations shown in Table 2 support the conclusion that there is a relatively high reproducibility of liquid sample transfer from the absorbent inoculation pad to the absorbent discs.

Example 3

Evaporation of Water from Small Disc during Incubation

The objective of this example was to determine the effect of position of the absorbent discs on water evaporation during incubation of the assay device. The small discs were expected to be most susceptible to loss of water during incubation and therefore were the focus of this example.

Figure 5A:
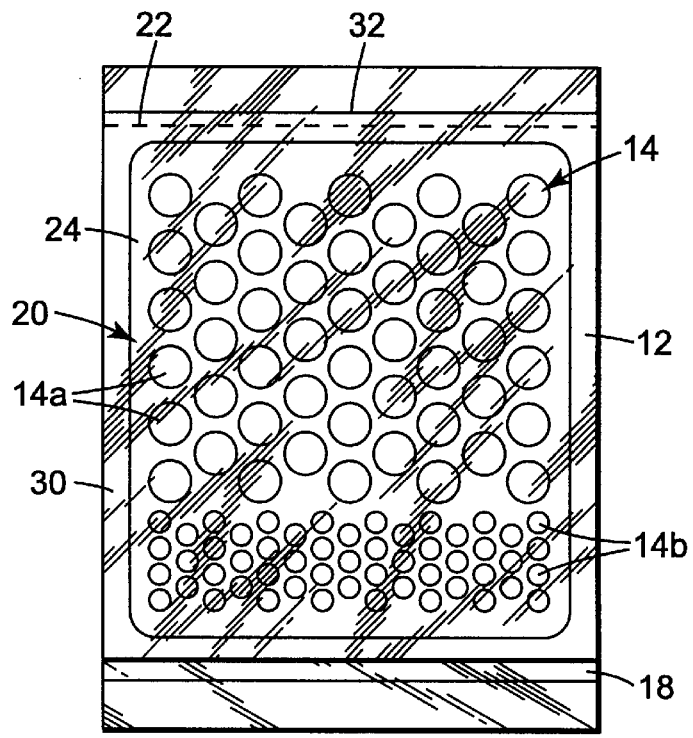
FIG. 5a is a top plan view of one configuration of a device of the present invention.
Figure 5B:
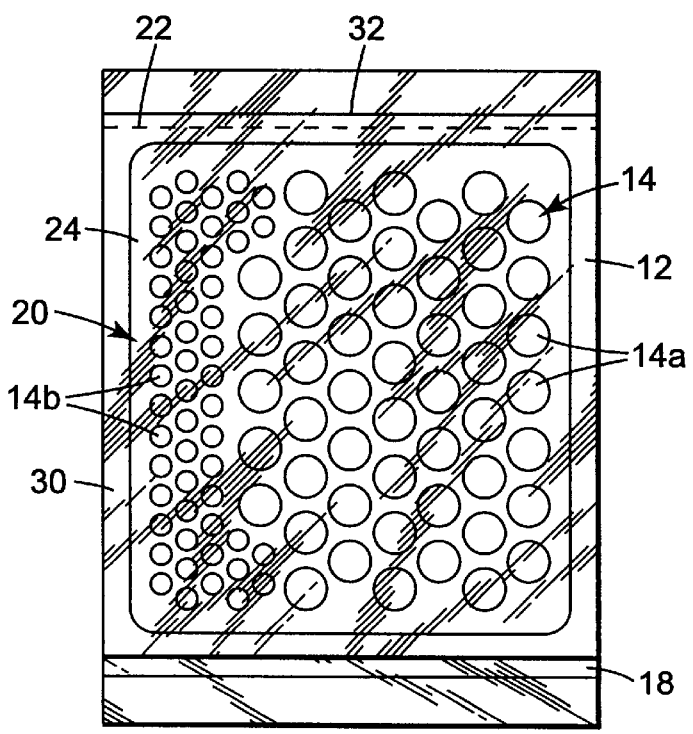
FIG. 5b is a top plan view of an alternative configuration of a device of the present invention.
Figure 5C:
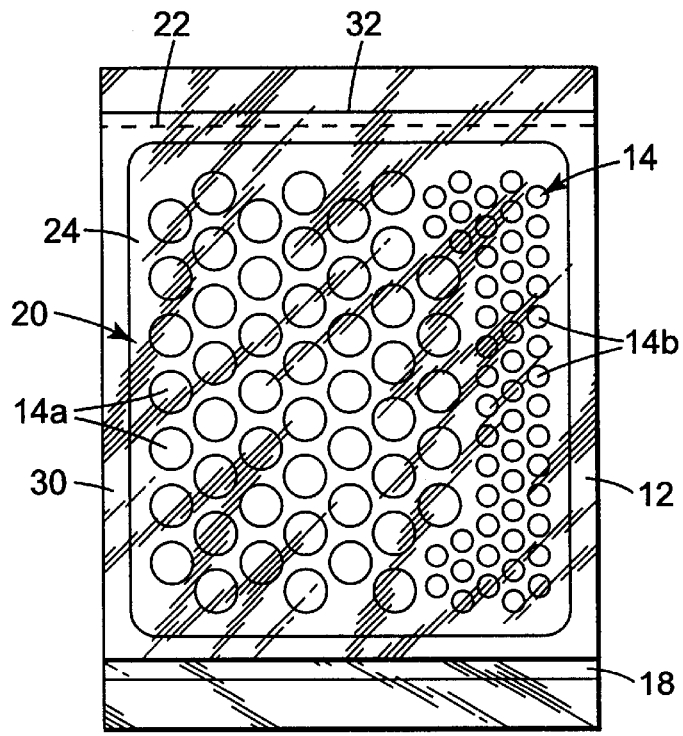
FIG. 5c is a top plan view of an alternative configuration of a device of the present invention.
Figure 5D:
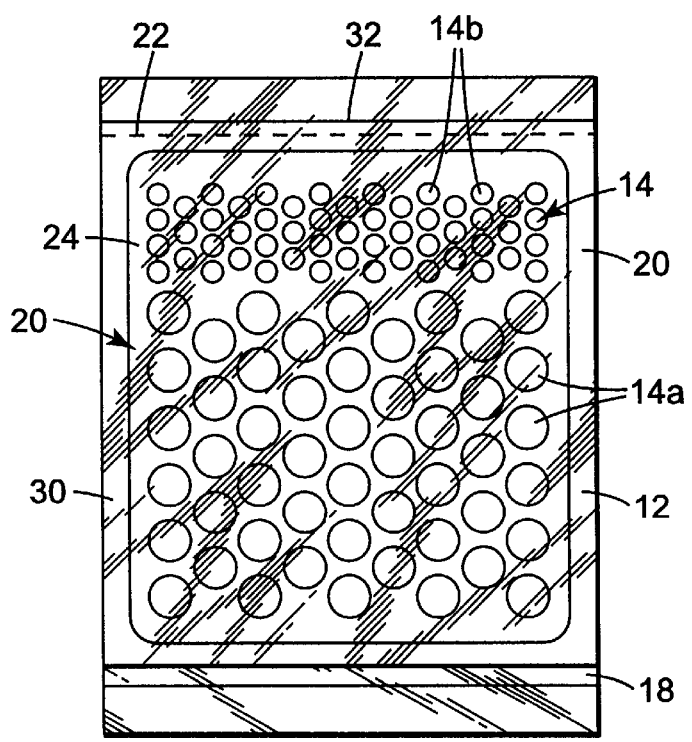
FIG. 5d is a top plan view of an alternative configuration of a device of the present invention.
Figure 5E:
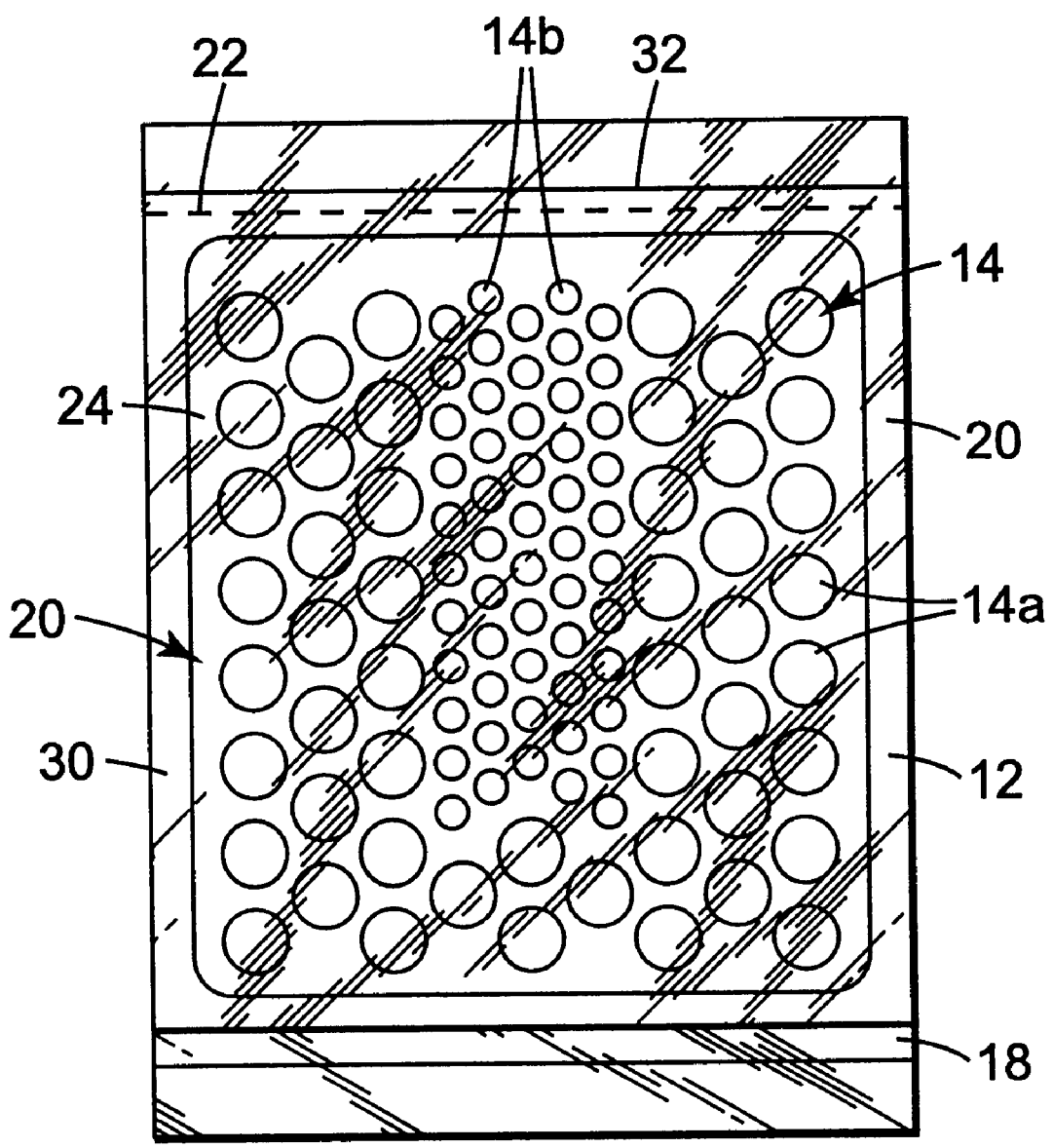
FIG. 5e is a top plan view of an alternative configuration of a device of the present invention.

Assay devices were constructed with each having 50 large discs and 52 small discs as described in Example 1, except that the orientation of large to small discs was varied in five different configurations as shown in FIG. 5a (Device A), FIG. 5b (Device B), FIG. 5c (Device C), FIG. 5d (Device D) and FIG. 5e (Device E). For each configuration, three assay devices were inoculated with a liquid sample (3.5 ml) of Butterfield's Buffer as described in Example 2. Immediately after inoculation, light absorbency reading of the small discs were measured as described in Example 2. The assay devices were then incubated for about 22 hours at room temperature (about 23° C.) and then light absorbency readings of the small discs were measured again. The differences between the initial (T=0) and the final (T=22) readings provided an indication of water loss from the small discs by evaporation during incubation. Results are shown in Table 3.

TABLE 3

Light Absorbency of Small Discs Before (T = 0) and After (T = 22) Incubation
[Average of 156 Discs with Background (Dry Disc Value) Subtracted]

|  | Device A | Device B | Device C | Device D | Device E |
|---|---|---|---|---|---|
| T = 0 hours | 0.306 ± 0.026 | 0.323 ± 0.031 | 0.311 ± 0.028 | 0.318 ± 0.027 | 0.343 ± 0.029 |
| T = 22 hours | 0.130 ± 0.156 | 0.211 ± 0.158 | 0.133 ± 0.159 | 0.178 ± 0.144 | 0.299 ± 0.067 |
| Difference | 0.176 ± 0.158 | 0.150 ± 0.156 | 0.178 ± 0.160 | 0.141 ± 0.146 | 0.044 ± 0.071 |

The data in Table 3 show that there were relatively large amounts of water loss during incubation from the small discs contained within assay devices A, B, C, and D; however, there was significantly less water loss within assay device E. The data also indicate a much higher variability of water loss, as evidenced by the standard deviations, from the assay configurations A, B, C, and D, compared to the water loss in configuration E.

Example 4

Detection and Enumeration of Microorganisms in a Milk Sample Using Absorbent Disc Assay Device The objective if this example was to utilize an absorbent disc assay device of this invention in order to detect and enumerate the number of microorganisms in a milk sample, and to compare the results with those obtained with a standard PETRIFILM™ Plate.

An assay device constructed as described in Example 1, except with 50 large discs and 53 small discs, was inoculated with a sample (about 3 ml) of Pasteurized skim milk as described in Example 2. As a reference, the skim milk sample was separately applied to two commercial Aerobic Count PETRIFILM™ Plates (3M Co., St. Paul, Minn.). The assay device and the PETRIFILM™ Plates were then incubated at 35° C. for 24 hours and 48 hours, respectively. The assay devices were enclosed in GLADLOCK ZIPPER™ storage bags (First Brands Corporation, Danbury, Conn.) during the incubation period.

The assay device was inspected following incubation and found to have 40 (out of 50) of the large discs show fluorescence under ultraviolet light and to have 9 (out of 53) small discs show fluorescence. The fluorescence on any disc indicates the presence of viable microorganisms on that disc. Using the formula Estimated MPN=(N/V)*ln(N/(N−X), where N is the total number of discs, V is the total volume of all of the discs and X is the number of discs that show a positive presence of microorganisms, an MPN of 93 colony forming units (cfu)/ml is calculated from the small discs and an MPN if 101 cfu/ml is calculated from the large discs. The consistency of these MPN results supports the utility of the assay device for the detection and enumeration of microorganisms in a food sample. These results were also consistent with the counts of 88 and 98 cfu/ml obtained with the two Aerobic Count PETRIFILM™ Plates.

Various modifications and alterations of this invention will be apparent to those skilled in the art without departing from the scope and spirit of this invention, and it should be understood that this invention is not limited to the illustrative embodiments set forth herein.

What is claimed is:

1. An assay device for detecting or enumeration of microorganisms, said device comprising: a substrate including absorbent discs attached thereto and an inoculation vehicle attached to said device wherein said inoculation vehicle is capable of coming into contact with said absorbent discs.

2. The device of claim 1 including a coversheet attached to said device.

3. The device of claim 1 wherein said inoculation vehicle is detachably attached to said device.

4. The device of claim 3 wherein said inoculation vehicle is attached to said device by a perforation.

5. The device of claim 1 wherein said inoculation vehicle comprises an absorbent pad.

6. The device of claim 3 wherein said inoculation vehicle comprises a thermoformed tray.

7. The device of claim 1 wherein said discs comprises two different sizes, each size capable of containing a different volume.

8. The device of claim 7 wherein said substrate includes an outer margin and the disc capable of containing a smaller volume of sample are grouped together on the substrate and as a group are substantially surrounded by discs capable of containing a larger volume of sample.

9. A method of using an assay device, comprising:
providing an assay device having a substrate including absorbent discs attached thereto and a disposable inoculation vehicle;
placing a sample on said inoculation vehicle;
placing said inoculation vehicle into contact with said absorbent discs to effect transfer of said sample from said vehicle to said discs; and
removing of said vehicle from said device.

10. The method of claim 9, further including incubating said device to grow microorganisms on said device.

11. The method of claim 10, further including detecting microorganisms on said device.

12. The method of claim 11, further including enumerating microorganisms.

13. The method of claim 11, wherein said method is conducted within twenty-four hours or less.

14. The method of claim 9, wherein said substrate includes discs of two different sizes.

15. The method of claim 9, wherein said inoculation vehicle comprises an absorbent pad.

* * * * *

UNITED STATES PATENT AND TRADEMARK OFFICE
CERTIFICATE OF CORRECTION

PATENT NO. : 6,291,202 B1
DATED : September 18, 2001
INVENTOR(S) : Peter D. Wickert and Michael G. Williams It is certified that error appears in the above-identified patent and that said Letters Patent is hereby corrected as shown below:

Column 6,
Line 44, delete the word "indicator" and insert in place thereof -- indicators --.
Line 59, delete the word "other" and insert in place thereof -- others --.

Column 7,
Line 67, delete the word "depend" and insert in place thereof -- depends --.

Column 8,
Line 7, delete the word "microscopocally" and insert in place thereof
-- microscopically --.

Column 11,
Line 60, before the word "skim" insert the word -- same --.

Column 12,
Line 21, delete the word "detecting" and insert in place thereof -- detection --.
Line 65, delete the word "of".

Signed and Sealed this

Twenty-first Day of May, 2002

Attest:

JAMES E. ROGAN
*Attesting Officer*      *Director of the United States Patent and Trademark Office*